(12) United States Patent
Guo et al.

(10) Patent No.: US 9,924,954 B2
(45) Date of Patent: Mar. 27, 2018

(54) HANDHELD POWER MACHINE FOR ORTHOPAEDIC DRILL AND SAW AND ORTHOPAEDIC DRILL AND SAW POWER SYSTEM WITH SAME

(71) Applicant: CHONGQING XISHAN SCIENCE & TECHNOLOGY CO., LTD., New North Zone, Chongqing (CN)

(72) Inventors: Yijun Guo, Chongqing (CN); Xinyun Zhang, Chongqing (CN); Changfeng Liu, Chongqing (CN)

(73) Assignee: Chongqing Xishan Science & Technology Co., Ltd., New North Zone, Chongqing (CN)

( * ) Notice: Subject to any disclaimer, the term of this patent is extended or adjusted under 35 U.S.C. 154(b) by 707 days.

(21) Appl. No.: 14/404,598

(22) PCT Filed: Apr. 16, 2013

(86) PCT No.: PCT/CN2013/074243
§ 371 (c)(1),
(2) Date: Nov. 28, 2014

(87) PCT Pub. No.: WO2014/082416
PCT Pub. Date: Jun. 5, 2014

(65) Prior Publication Data
US 2015/0245846 A1 Sep. 3, 2015

(30) Foreign Application Priority Data
Nov. 28, 2012 (CN) .......................... 2012 1 0494930

(51) Int. Cl.
*A61B 17/16* (2006.01)
*F41A 17/52* (2006.01)
(Continued)

(52) U.S. Cl.
CPC .......... *A61B 17/1662* (2013.01); *A61B 17/14* (2013.01); *A61B 17/1622* (2013.01);
(Continued)

(58) Field of Classification Search
CPC ............................ F41A 17/52; A61B 17/1626
See application file for complete search history.

(56) References Cited

U.S. PATENT DOCUMENTS 6,406,280 B1   6/2002 Pfeiffer et al.
6,958,071 B2 * 10/2005 Carusillo ......... A61B 17/32002
                                                606/170
(Continued)

FOREIGN PATENT DOCUMENTS

CN   2103993 U   5/1992
CN   2334346 Y   8/1999
(Continued)

OTHER PUBLICATIONS

Chinese First Office Action, Chinese Application No. 201210494930.8, dated Jun. 30, 2014, 7 pages (with English summary).
(Continued)

*Primary Examiner* — David Bates
(74) *Attorney, Agent, or Firm* — Fenwick & West LLP

(57) ABSTRACT

The power handpiece for orthopedic drilling and sawing according to the present application at least includes a handle housing, a clamping assembly for clamping a cutting tool assembly, a power motor for outputting power and driving the cutting tool assembly to perform drilling and sawing operations, and a switch assembly for controlling power output of the power motor, wherein the power motor is connected to an external power source. The power machine utilizes an external power source which can be a large-scale accumulator or city electricity, thereby avoiding
(Continued)

the situation of power failure or low power which is prone to occur in the operation, and ensuring the smooth performance of the operation, reduce the quantity of heat of the handle, reduce the overall weight of the device, make the device portable and easy to operate, and improve the efficiency of the operation.

16 Claims, 3 Drawing Sheets

(51) Int. Cl.
    *A61B 17/14* (2006.01)
    *A61B 17/00* (2006.01)
(52) U.S. Cl.
    CPC .............. *A61B 17/1628* (2013.01); *A61B 2017/00464* (2013.01); *F41A 17/52* (2013.01)

(56) References Cited

U.S. PATENT DOCUMENTS

2002/0165549 A1 11/2002 Owusu-Akyaw et al.
2007/0085496 A1* 4/2007 Philipp ................ A61B 17/151
                                                            318/139
2010/0061181 A1 3/2010 Malackowski et al.

FOREIGN PATENT DOCUMENTS

| CN | 2388923 Y | 7/2000 |
| CN | 201079409 Y | 7/2008 |
| CN | 101507649 A | 8/2009 |
| CN | 101530341 A | 9/2009 |
| CN | 201692053 U | 1/2011 |
| CN | 201930027 U | 8/2011 |
| CN | 102213968 A | 10/2011 |
| CN | 102940516 A | 2/2013 |
| CN | 202723940 U | 2/2013 |
| CN | 202960652 U | 6/2013 |
| WO | WO 02/087422 A2 | 11/2002 |

OTHER PUBLICATIONS

PCT International Search Report and Written Opinion, PCT/CN2013/074243, dated Sep. 5, 2013, 15 Pages. (with English translation of PCT International Search Report).

* cited by examiner

HANDHELD POWER MACHINE FOR ORTHOPAEDIC DRILL AND SAW AND ORTHOPAEDIC DRILL AND SAW POWER SYSTEM WITH SAME

This application claims the benefit of priority to Chinese patent application No. 201210494930.8 titled "POWER HANDPIECE FOR ORTHOPAEDIC DRILLING AND SAWING" and filed with the Chinese State Intellectual Property Office on Nov. 28, 2012, which is incorporated herein by reference in its entirety.

TECHNICAL FIELD

The present application relates to medical apparatus and instruments, particularly to a power handpiece for orthopaedic drilling and sawing and a power system for orthopaedic drilling and sawing with the power handpiece used in surgical operations.

BACKGROUND

Orthopaedic drilling and sawing operation are common surgical manners and are performed by an orthopaedic drilling and sawing device (for example, a handpiece). In the conventional technology, the orthopaedic drilling and sawing device generally has a handpiece structure, which includes a housing, a driving motor arranged in the housing, a clamping assembly, a control switch, and an accumulator for providing power source, and the handpiece structure is easy to operate and can perform drilling and sawing operations by switching a necessary switch. However, since the drilling and sawing device with such structure uses the accumulator, and the time of endurance of the accumulator is limited by the structure of the device. Thus, during the operation, the situation of power failure or low power is prone to occur, which affects the performing of the operation or even cause an accident. Moreover, due to the accumulator, the device not only generates a high quantity of heat which may destroy circuits, but also has a greater weight, thus it is difficult to operate, which indirectly reduces the efficiency of the operation.

Therefore, it is required to improve the existing driving device (i.e. the handpiece) for orthopaedic drilling and sawing, to avoid the situation of power failure or low power which is prone to occur in the operation, and to ensure the smooth performance of the operation, reduce the quantity of heat of the handle, reduce the overall weight of the device, make the device portable and easy to operate, and improve the efficiency of the operation.

SUMMARY

In view of this, a power handpiece for orthopaedic drilling and sawing is provided according to the present application, to avoid the situation of power failure or low power which is prone to occur in the operation, and to ensure the smooth performance of the operation, reduce the quantity of heat of the handle, reduce the overall weight of the device, make the device portable and easy to operate, and improve the efficiency of the operation. On this basis, a power system for orthopaedic drilling and sawing having the power handpiece is further provided according to the present application.

The power handpiece for orthopaedic drilling and sawing according to the present application at least includes a handle housing, a clamping assembly for clamping a cutting tool assembly, a power motor for outputting power and driving the cutting tool assembly to perform drilling and sawing operations, and a switch assembly for controlling power output of the power motor, wherein the power motor is connected to an external power source.

Further, the power motor is connected to an external control system configured to control an operating state of the power motor by the switch assembly, and the control system is configured to drive the power motor to positively rotate, reversely rotate and reciprocately rotate via the switch assembly.

Further, a rotor shaft of the power motor is an axially hollow rotor shaft, a transmission claw drivably connected to the cutting tool assembly is provided and is drivably connected to the rotor shaft, and the hollow rotor shaft is in communication with the transmission claw axially.

Further, the switch assembly at least includes a button guide rod, a guide rod control mechanism and a button guide rod sensing member;

two button guide rods are provided, and are arranged in respective guide rod seats, and the two button guide rods are reciprocately slidable along axes of the respective guide rod seats; a radial through hole is provided on a side wall of a guide channel of each of the guide rod seats, and the guide channel of the guide rod seat is configured to be passed through by the respective button guide rod, and a slidable roller is arranged in the radial through hole, a length of the radial through hole is smaller than a diameter of the roller, and the button guide rod is configured to be axially locked by sliding inwardly with the roller;

the guide rod control mechanism includes a shifting block rotatable about an axis parallel to the button guide rods, the rollers of the two button guide rods are arranged to directly face to the shifting block, the shifting block is provided with two circumferential wave-shaped portions corresponding to the rollers, and the circumferential wave-shaped portions are configured to be driven by rotation of the shifting block to drive the rollers to slide along the respective radial through holes;

the structure of the two circumferential wave-shaped portions are configured to drive the rollers at two sides thereof to simultaneously lock the respective button guide rods, to simultaneously release the respective button guide rods, or to lock one of the button guide rods and release the other of the button guide rods at one time; and the button guide rod sensing member is configured to collect movement signals of the two button guide rods and send the collected movement signals to the external control system.

Further, the two button guide rods are symmetrically disposed at two sides of the shifting block, and the two circumferential wave-shaped portions are provided with crests which are radially opposite to each other, troughs which are radially opposite to each other, and a crest and a trough which are radially opposite to each other.

Further, a guide rod bush is fixedly provided on the button guide rod axially, and a return spring is arranged between the guide rod seat and the guide rod bush to apply a return pretension force to the guide rod seat; a side wall of the guide rod bush is provided with an axial groove, a guide screw is radially screwed into the side wall of the guide channel of the guide rod seat to extend into the axial groove, and an axial bottom of the axial groove is a blind end abutting against the guide screw by the pretension force of the return spring; and the guide rod bush is provided with a locking recess for cooperating with the roller to axially lock the button guide rod.

Further, the guide rod seats are fixedly arranged in a switch seat, a shifting block spindle is provided along an axis of the shifting block, and the shifting block spindle is arranged in the switch seat and is configured to rotatably cooperate with the switch seat; and the switch seat is hermetically fixed in the handle housing, the button guide rod extends inwardly to the handle housing and protrudes out of the respective guide rod seat, an end of the button guide rod that protrudes out of the guide rod seat is provided with a sensing head, and the button guide rod sensing member is a sensing circuit board which is located in the handle housing and fixedly connected to the switch seat, and is corresponding to the sensing head.

Further, the handle housing is provided with a handheld portion, a cable seat configured for leading in a cable and restraining the same is fixedly connected to a tail end of the handheld portion, a lateral side of an outer surface of a front end of the cable seat is provided with a dovetail sunk platform, and an inner surface of the tail end of the handheld portion is provided with a dovetail sunk groove configured to be interlocked with the dovetail sunk platform; and another lateral side of the outer surface of the front end of the cable seat is fixedly connected to the tail end of the handheld portion via a screw.

Further, the power motor is mounted in the handle housing, and a liner tube is coaxially arranged in the hollow shaft of the power motor; and a front end of a claw of the transmission claw has a triangular tooth-shaped structure.

A power system for orthopeadic drilling and sawing according to the present application includes a host, a foot controller connected to the host, and a power handpiece for orthopeadic drilling and sawing connected to the host, wherein the power handpiece for orthopeadic drilling and sawing is the above-described power handpiece for orthopeadic drilling and sawing.

The present application has the following beneficial effects. In the power handpiece for orthopeadic drilling and sawing according to the present application, the power machine utilizes an external power source which can be a large-scale accumulator or city electricity, thereby avoiding the situation of power failure or low power which is prone to occur in the operation, and ensuring the smooth performance of the operation, reduce the quantity of heat of the handle, reduce the overall weight of the device, make the device portable and easy to operate, and improve the efficiency of the operation.

BRIEF DESCRIPTION OF THE DRAWINGS

The present application is further described in conjunction with drawings and embodiments hereinafter.

DETAILED DESCRIPTION

The technical solutions in the embodiments of the present application will be described clearly and completely hereinafter in conjunction with the drawings in the embodiments of the present application. Apparently, the described embodiments are only a part of the embodiments of the present application, rather than all embodiments. Based on the embodiments in the present application, all of other embodiments, made by the person skilled in the art without any creative efforts, fall into the scope of the present application.

Embodiments of the present application will be described in detail in conjunction with drawings.

Figure 1:
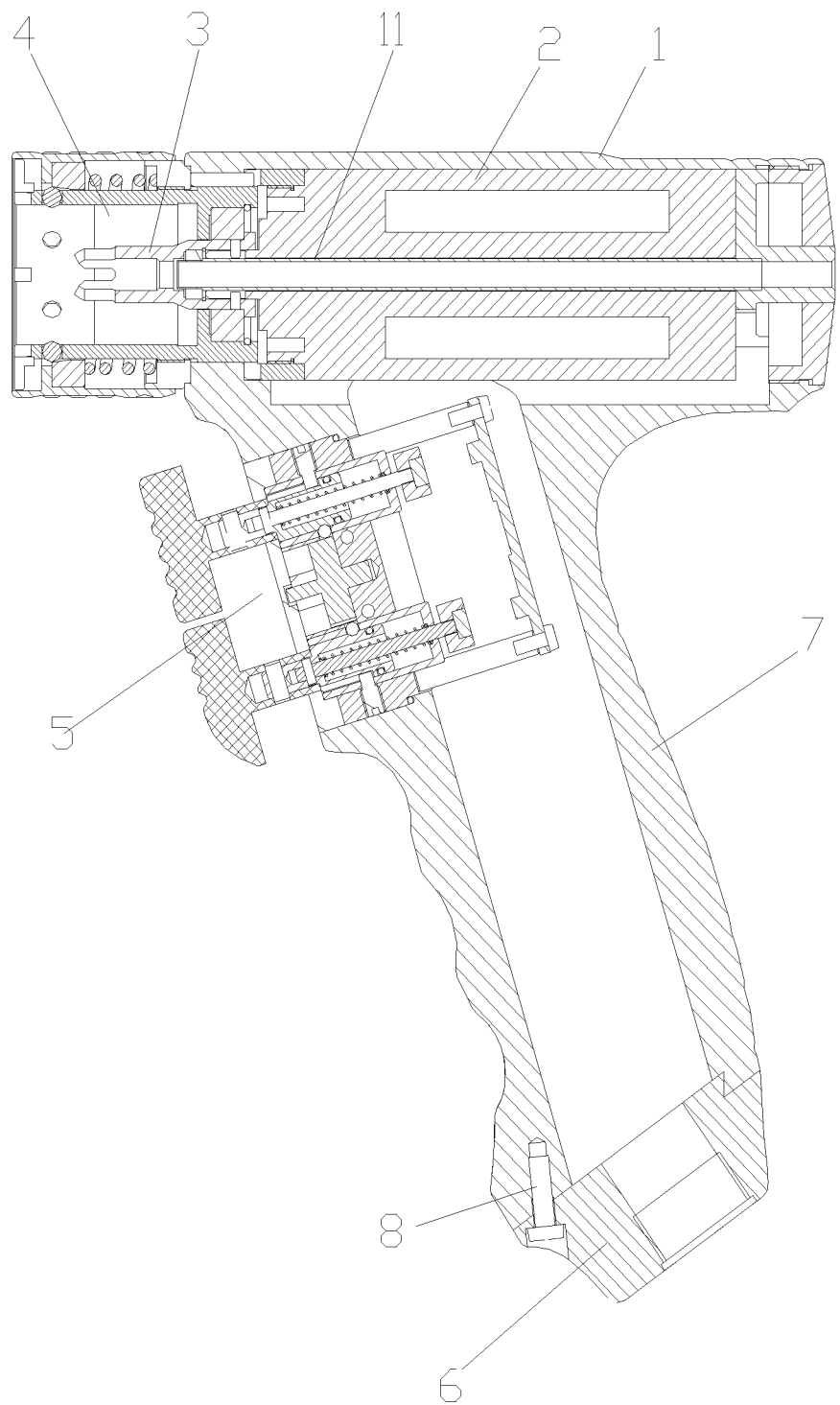
FIG. 1 is a schematic view showing the structure of a power handpiece for orthopaedic drilling and sawing according to the present application.
Figure 2:
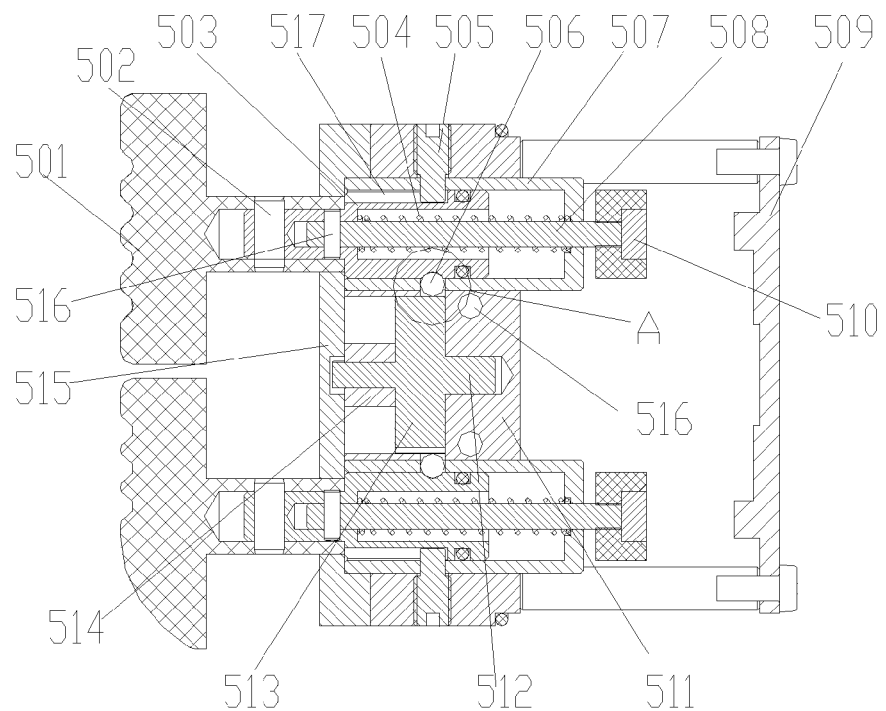
FIG. 2 is a schematic view showing the structure of a switch assembly according to the present application.
Figure 3:
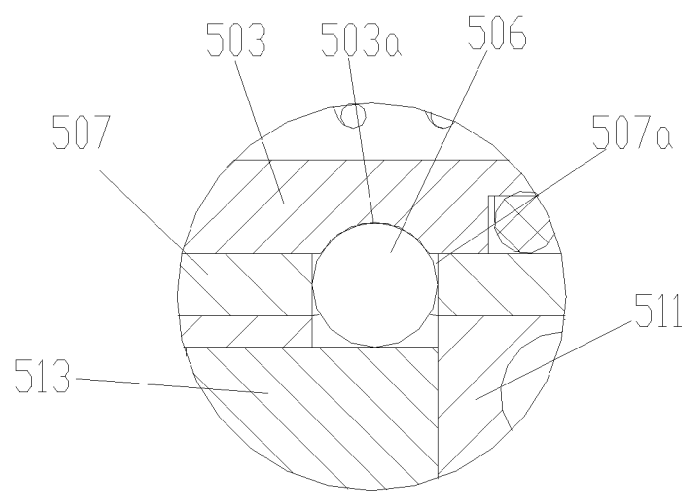
FIG. 3 is an enlarged view of part A in FIG. 2.
Figure 4:
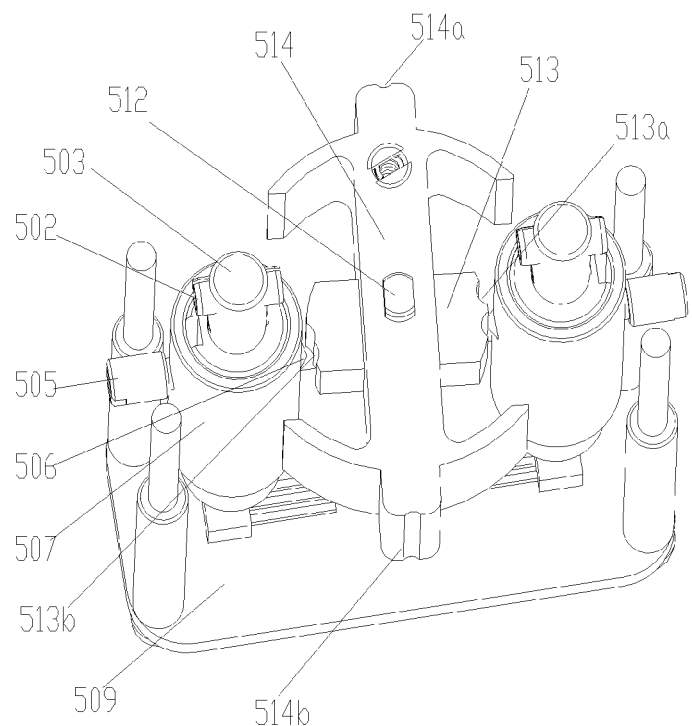
FIG. 4 is a perspective view showing the structure of the switch assembly according to the present application.

FIG. 1 is a schematic view showing the structure of the present application; FIG. 2 is a schematic view showing the structure of a switch assembly according to the present application; FIG. 3 is an enlarged view of part A in FIG. 2; and FIG. 4 is a perspective view showing the structure of the switch assembly according to the present application.

As shown in the Figures, a power handpiece for orthopaedic drilling and sawing according to this embodiment at least includes a handle housing 1, a clamping assembly 4 for clamping a cutting tool assembly, a power motor 2 for outputting power and driving the cutting tool assembly to perform drilling and sawing operations, and a switch assembly 5 for controlling the power output of the power motor 2, wherein the power motor 2 is connected to an external power source. Generally, the cutting tool assembly includes a cutting tool, a cutting tool transmission component and a mounting clamping seat. The clamping assembly 4 is a part assembly for mounting the cutting tool assembly and may employ any conventional mechanical structures which can realize the clamping function. Since the cutting tools generally have universal clamping structures and may mostly use an elastic clamping structure as shown in the figure, wherein, a front-end roller locking mechanism is employed to fix various functional machine heads to realize a reliable connection, which belongs to the conventional technology, thus will not be described herein.

In this embodiment, the power motor 2 is connected to an external control system configured to control an operating state of the power motor 2 by the switch assembly 5. The control system is configured to drive the power motor 2 to rotate positively, rotate reversely and rotate reciprocately, via the switch assembly. With the external power source and the external control system and by setting an established process, the control system can control the power motor to achieve the above movements according to an instruction from the switch assembly, to adapt to actions required in an orthopedic surgery, thereby changing the current situation of single function and simple action in the conventional technology. The control system is a control unit having a central processing unit and can be achieved by an electrical automatic control structure in the conventional technology.

In this embodiment, the power motor 2 has a rotor shaft which is an axially hollow rotor shaft, a transmission claw 3 drivably connected to the cutting tool assembly is provided and is drivably connected to the rotor shaft, and the hollow rotor shaft is in communication with the transmission claw 3 axially. With the structure of the hollow rotor shaft, the present application has a good universality and can be used for driving a longer cutting tool assembly such as a kirschner wire. Of course, the power handpiece in this solution can also drive various machine heads 40 of other forms, which include a horizontal swing saw machine head, a reciprocating saw machine head, a sternum saw machine head, a drill chuck, a reaming and filing machine head, a kirschner wire chuck and the like, thus a doctor can select various machine heads according to the requirement of an operation procedure, so as to achieve "one machine with multiple heads", and requirements for most orthopedic surgeries can be satisfied by attaching various terminal cutting tools.

In this embodiment, the switch assembly 5 at least includes a button guide rod 508, a guide rod control mechanism and a button guide rod sensing member 509.

Two button guide rods 508 are provided, and are arranged in two guide rod seats 507 respectively, and the two button guide rods 508 are each reciprocately slidable along the axe of the respective guide rod seat 507. A radial through hole 507a is provided on a side wall of a guide channel of the guide rod seat 507, and the guide channel of the guide rod seat 507 is configured to be passed through by the button guide rod 508, and a slidable roller 506 is arranged in the radial through hole. A length of the radial through hole 507a is smaller than a diameter of the roller 506, and the button guide rod 508 can be axially locked by sliding inwardly with the roller 506. The two button guide rods 508 of the switch assembly have the same structure as well as corresponding components thereof, thus are referred to with same reference numerals.

The guide rod control mechanism includes a shifting block 513 rotatable about an axis parallel to the button guide rods 508, the rollers 506 of the two button guide rods 508 are arranged to directly face to the shifting block 513, the shifting block 513 is provided with two circumferential wave-shaped portions 513a and 513b corresponding to the rollers 506, and the circumferential wave-shaped portions 513a and 513b are configured to be driven by rotation of the shifting block 513 to drive the rollers 506 to slide along the radial through holes 507a.

With the structure of the two circumferential wave-shaped portions 513a, the rollers 506 at two sides of the circumferential wave-shaped portions are driven to simultaneously lock the respective button guide rods 508, to simultaneously release the respective button guide rods 508, or to lock one of the button guide rods 508 and release the other of the button guide rods 508 at one time. A sensing member of the button guide rods 508 is adapted to collect movement signals of the two button guide rods 508 and send the collected movement signals to an external control system. According to the collected movement signals of the two button guide rods 508, the control system sends a rotation instruction to the power motor, to enable the power motor to have four operating states according to the movement signals of the button guide rods 508, and the four operating states include a full locked state, a positive rotating state, a reverse rotating state, and a reciprocating rotating state, and in this way, the purpose of the present application is realized. The reciprocating movement of the two button guide rods can be controlled by the cooperation between the two circumferential wave-shaped portions 513a and the rollers of the two button guide rods. Specifically, the full locked state is a state that crests of the two circumferential wave-shaped portions 513a, 513b simultaneously act on the rollers of the two button guide rods, and in this state, the two button guide rods 508 cannot move. The crest of one of the circumferential wave-shaped portions 513a, 513b acts on the roller of the respective button guide rod, thus this button guide rod is locked and cannot move, and a trough of the other of the circumferential wave-shaped portions 513a, 513b is aligned with the roller of the other button guide rod, thus this button guide rod is movable, in other words, the movement control system sends a signal to drive the power motor to positively rotate or reversely rotate, and vice versa. The full unlocked state is a state that the troughs of the two circumferential wave-shaped portions simultaneously act on the rollers of the two button guide rods, and in this state, the two button guide rods can be pressed at the same time and can move, to send a signal to the movement control system and drive the power motor to reciprocately rotate. Of course, procedures set in the control system are required to realize the above processes.

In this embodiment, the two button guide rods 508 are symmetrically disposed at two sides of the shifting block, and the two circumferential wave-shaped portions 513a, 513b are provided with crests which are radially opposite to each other, troughs which are radially opposite to each other, and a crest and a trough which are radially opposite to each other. With such symmetrical structure, the switch assembly according to the present application has a compact structure, the circumferential wave-shaped portions of the shifting block are easy to produce, and the four operating states can be easily achieved.

In this embodiment, a guide rod bush 503 is fixedly provided on the button guide rod 508 axially. As shown in the figures, the button guide rod 508 and the guide rod bush 503 are connected by a shaft pin 516 passing through the two members radially. A return spring 504 is arranged between the guide rod seat 507 and the guide rod bush 503 to apply a return pretension force to the guide rod seat. As shown in the figures, the return spring 504 is sleeved on the guide rod bush of the button guide rod 508, and has two ends abutting against a bottom of the guide rod seat 507 and a step formed by an inner hole of the guide rod bush 503, respectively. The guide rod bush 503 also functions as a spring seat of the button guide rod. A side wall of the guide rod bush 503 is provided with an axial groove 517. A guide screw 505 is radially screwed into the side wall of the guide channel of the guide rod seat 507 to extend into the axial groove 517. An axial bottom of the axial groove 517 is a blind end abutting against the guide screw 505 by the pretension force of the return spring 504. The guide rod bush 503 is provided with a locking recess 503a for cooperating with the roller 506 to axially lock the button guide rod 508, i.e., the roller 506 moves radially to be embedded into the locking recess 503a of the respective guide rod bush 503, thereby axially locking the button guide rod 508. As shown in the figures, a button 501 is provided to cooperate with the guide rod bush 503, the button 501 is provided with a channel, thus the button 501 can be sleeved on the guide rod bush 503, and the button 501 and the guide rod bush 503 are connected by a shaft pin 502 radially passing through the two members.

In this embodiment, the guide rod seats 507 are fixedly arranged in a switch seat 511. As shown in the figures, the switch seat 511 and the guide rod seat 507 are axially fixed by the guide screw 505 passing through the two members, and are tightly pressed by a pressing cover 515 to form a necessary fixed connection. Of course, the fixing manner can be any existing mechanical fixing manners which can achieve the fixing connection. A shifting block spindle 512 is provided along an axis of the shifting block 513, and in this embodiment, the shifting block spindle 512 and the shifting block 513 are integrally formed. The shifting block spindle 512 is arranged in the switch seat 511 and is configured to rotatably cooperate with the switch seat 511. As shown in the figures, the shifting block spindle 512 extends into a shaft hole formed in the switch seat 511 to rotatably cooperate with the switch seat 511. The shifting block 513 is required to have a driving handle, and as shown in the figures, a shifting block driving handle 514 is provided and is fixedly connected to the shifting block spindle 512 in a circumferential direction. The shifting block driving handle 514 is symmetrical with respect to the axis of the shifting block spindle 512, and has two ends forming driving ends respectively. In operation, the two driving ends can be driven by two fingers simultaneously, thus the shifting block can be operated stably. Of course, in order to increase the discontinuous feeling during driving the shifting block driving handle 514 and increase the hand feeling of the operator, the shifting block may be provided with a gear position structure and a spring, which belong to the conventional technology and will not be described herein.

The switch seat 511 is hermetically fixed in the handle housing 1. During the assembly, necessary sealing members are arranged, such as an O-ring, and are indicated in the figures, and these sealing members are conventional sealing structures which will not be described herein. The fixed connection can be achieved by a simple pin connection structure, and for example, a pin shaft 516 as shown in the figures is manufactured for the pin connection. The button guide rod 508 extends inwardly to the handle housing 1 and protrudes out of the guide rod seat 507, an end of the button guide rod 508 that protrudes out of the guide rod seat 507 is provided with a sensing head 510. The button guide rod sensing member 509 may be a sensing circuit board which is located in the handle housing 2 and fixedly connected to the switch seat 511, and is corresponding to the sensing head 510. The sensing head 510 and the sensing circuit board can employ existing normal structures to achieve the purpose, for example a proximity switch system (using magnetic induction, and etc.), a holl sensor system and the like, which belong to the conventional technology and will not be described herein. In other words, the button of the switch assembly can be controlled by the holl sensor, to steplessly regulate the control system to drive the power motor to positively rotate, reversely rotate and reciprocately rotate via the switch assembly.

In this embodiment, the handle housing 1 is provided with a handheld portion 7. A cable seat 6 configured for leading in a cable and restraining the same is fixedly connected to the tail end of the handheld portion 7. A lateral side of an outer surface of a front end of the cable seat 6 is provided with a dovetail sunk platform, and an inner surface of the tail end of the handheld portion is provided with a dovetail sunk groove configured to be interlocked with the dovetail sunk platform. The other lateral side of the outer surface of the front end of the cable seat is fixedly connected to the tail end of the handheld portion via a screw 8. With such interlocked dovetail pair structure, during the assembly, only one side is required to be fitted and the other side is fixed via one screw 8, which is simple and easy to perform.

In this embodiment, the power motor 2 is mounted in the handle housing 1. A liner tube 11 is coaxially arranged in the hollow shaft of the power motor 2, to prevent a high-speed friction between the inner hole of the hollow power shaft and the cutting tool deeply extending into the hollow shaft, such as the kirschner wire. A front end of a claw of the transmission claw 3 has a triangular tooth-shaped structure, and in assembly, such structure has a good adaptability with splines of the tail of the cutting tool, thus the assembly and transmission can be achieved without alignment.

According to the above description of the structure and control principle, in the present application, under the control of the external power source and the external control system and in conjunction with the structure of the double-button switch, four operating states can be achieved, which include a full locked state, a positively rotating state, a reversely rotating state, and a reciprocating rotating state. Compared to the conventional technology, the present application has a small volume, a light weight and a small calorific value and can ensure that the smooth performance of the operation. Furthermore, the operating state can be regulated as desired, thereby facilitating the operation and ensuring therapeutic effect.

Figure 5:
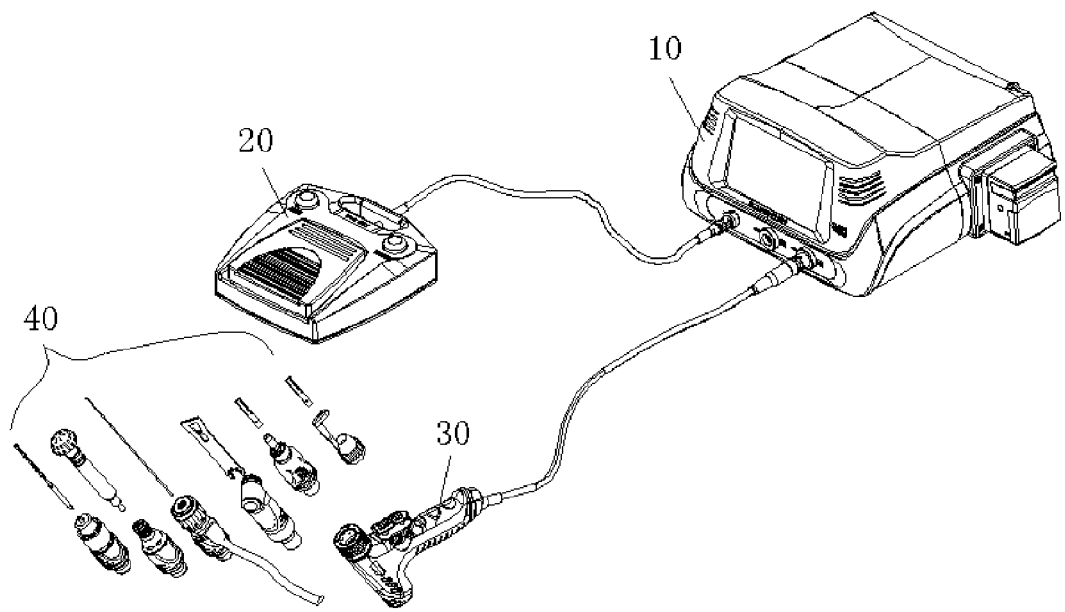
FIG. 5 is a schematic view showing the overall structure of a power system for orthopaedic drilling and sawing.

Besides the above power handpiece for orthopaedic drilling and sawing, a power system for orthopaedic drilling and sawing having the power handpiece is further provided according to this embodiment. Reference is made to FIG. 5, which is a schematic drawing showing the overall structure of the power system for orthopaedic drilling and sawing according to the present application.

The power system for orthopaedic drilling and sawing includes a host 10, a foot controller 20 connected to the host 10, a power handpiece 30 for orthopaedic drilling and sawing connected to the host 10, and respective machine heads 40 required for various functions. The power handpiece 30 for orthopaedic drilling and sawing is the above-described power handpiece for orthopaedic drilling and sawing. During the operation, the doctor can output a relevant operating instruction by the switch assembly 5 on the power handpiece for orthopaedic drilling and sawing, or output the same operating instruction by a foot switch on the foot controller 20, and then control the operating state of the power motor 2 by the control system arranged on the host 10.

It should be noted that, specific configurations of the foot controller 20 and the host 10 can be achieved based on the conventional technology, thus will not be described herein. It should be appreciated that, any system using the power handpiece for orthopaedic drilling and sawing according to the present application falls in the scope of the present application.

The embodiments described hereinabove are only preferred embodiments of the present application. It should be noted that, for the person skilled in the art, a few of modifications and improvements may be made without departing from the principle of the present application, and these modifications and improvements are deemed to fall into the scope of the present application.

The invention claimed is:

1. A power handpiece for orthopaedic drilling and sawing, at least comprising:
a handle housing, a clamping assembly for clamping a cutting tool assembly, a power motor for outputting power and driving the cutting tool assembly to perform drilling and sawing operations, and a switch assembly for controlling power output of the power motor, wherein the power motor is connected to a power source external to the power motor,
wherein the power motor is connected to a control system external to the power motor configured to control an operating state of the power motor by the switch assembly,
wherein the switch assembly at least comprises a button guide rod, a guide rod control mechanism and a button guide rod sensing member,
two button guide rods are provided, and are arranged in respective guide rod seats, and the two button guide rods are reciprocately slidable along axes of the respective guide rod seats;
a radial through hole is provided on a side wall of a guide channel of each of the guide rod seats, and the guide channel of the guide rod seat is configured to be passed through by the respective button guide rod, and a slidable roller is arranged in the radial through hole, a length of the radial through hole is smaller than a diameter of the roller, and the button guide rod is configured to be axially locked by sliding inwardly with the roller, the guide rod control mechanism comprises a shifting block rotatable about an axis parallel to the button guide rods, the rollers of the two button guide rods are arranged to directly face to the shifting block, the shifting block is provided with two circumferential wave-shaped portions corresponding to the rollers, and the circumferential wave-shaped portions are configured to be driven by rotation of the shifting block to drive the rollers to slide along the respective radial through holes, the structure of the two circumferential wave-shaped portions are configured to drive the rollers at two sides thereof to simultaneously lock the respective button guide rods, to simultaneously release the respective button guide rods, or to lock one of the button guide rods and release the other of the button guide rods at one time, and the button guide rod sensing member is configured to collect movement signals of the two button guide rods and send the collected movement signals to the control system external to the power motor.

2. The power handpiece for orthopaedic drilling and sawing according to claim 1, wherein the switch assembly has a button controlled by a hall sensor, and is configured to regulate the control system in a stepless manner to drive the power motor to positively rotate, reversely rotate and reciprocately rotate.

3. The power handpiece for orthopaedic drilling and sawing according to claim 1, wherein a rotor shaft of the power motor is an axially hollow rotor shaft, a transmission claw configured to be drivably connected to the cutting tool assembly is provided and is drivably connected to the rotor shaft, and the hollow rotor shaft is in communication with the transmission claw axially.

4. The power handpiece for orthopaedic drilling and sawing according to claim 1, wherein the two button guide rods are symmetrically disposed at two sides of the shifting block, and the two circumferential wave-shaped portions are provided with crests which are radially opposite to each other, troughs which are radially opposite to each other, and a crest and a trough which are radially opposite to each other.

5. The power handpiece for orthopaedic drilling and sawing according to claim 1, wherein a guide rod bush is fixedly provided on the button guide rod axially, and a return spring is arranged between the guide rod seat and the guide rod bush to apply a return pretension force to the guide rod seat; a side wall of the guide rod bush is provided with an axial groove, a guide screw is radially screwed into the side wall of the guide channel of the guide rod seat to extend into the axial groove, and an axial bottom of the axial groove is a blind end abutting against the guide screw by the pretension force of the return spring; and the guide rod bush is provided with a locking recess for cooperating with the roller to axially lock the button guide rod.

6. The power handpiece for orthopaedic drilling and sawing according to claim 1, wherein the guide rod seats are fixedly arranged in a switch seat, a shifting block spindle is provided along an axis of the shifting block, and the shifting block spindle is arranged in the switch seat and is configured to rotatably cooperate with the switch seat; a shifting block driving handle is provided and is fixedly connected to the shifting block spindle in a circumferential direction, and the shifting block driving handle has two ends being symmetrical with respect to the axis of the shifting block spindle and forming driving ends respectively; and the switch seat is hermetically fixed in the handle housing, the button guide rod extends inwardly to the handle housing and protrudes out of the respective guide rod seat, an end of the button guide rod that protrudes out of the guide rod seat is provided with a sensing head, and the button guide rod sensing member is a sensing circuit board which is located in the handle housing and fixedly connected to the switch seat, and is corresponding to the sensing head.

7. The power handpiece for orthopaedic drilling and sawing according to claim 6, wherein the handle housing is provided with a handheld portion, a cable seat configured for leading in a cable and restraining the same is fixedly connected to a tail end of the handheld portion, a lateral side of an outer surface of a front end of the cable seat is provided with a dovetail sunk platform, and an inner surface of the tail end of the handheld portion is provided with a dovetail sunk groove configured to be interlocked with the dovetail sunk platform; and another lateral side of the outer surface of the front end of the cable seat is fixedly connected to the tail end of the handheld portion via a screw.

8. The power handpiece for orthopaedic drilling and sawing according to claim 3, wherein the power motor is mounted in the handle housing, and a liner tube is coaxially arranged in the hollow shaft of the power motor; and a front end of a claw of the transmission claw has a triangular tooth-shaped structure.

9. A power system for orthopeadic drilling and sawing, comprising a host, a foot controller connected to the host, and a power handpiece for orthopeadic drilling and sawing connected to the host, wherein the power handpiece for orthopeadic drilling and sawing is the power handpiece for orthopeadic drilling and sawing according to claim 1.

10. The power system for orthopeadic drilling and sawing according to claim 9, wherein the switch assembly has a button controlled by a hall sensor, and is configured to regulate the control system in a stepless manner to drive the power motor to positively rotate, reversely rotate and reciprocately rotate.

11. The power system for orthopeadic drilling and sawing according to claim 9, wherein a rotor shaft of the power motor is an axially hollow rotor shaft, a transmission claw configured to be drivably connected to the cutting tool assembly is provided and is drivably connected to the rotor shaft, and the hollow rotor shaft is in communication with the transmission claw axially.

12. The power system for orthopeadic drilling and sawing according to claim 9, wherein the two button guide rods are symmetrically disposed at two sides of the shifting block, and the two circumferential wave-shaped portions are provided with crests which are radially opposite to each other, troughs which are radially opposite to each other, and a crest and a trough which are radially opposite to each other.

13. The power system for orthopeadic drilling and sawing according to claim 9, wherein a guide rod bush is fixedly provided on the button guide rod axially, and a return spring is arranged between the guide rod seat and the guide rod bush to apply a return pretension force to the guide rod seat; a side wall of the guide rod bush is provided with an axial groove, a guide screw is radially screwed into the side wall of the guide channel of the guide rod seat to extend into the axial groove, and an axial bottom of the axial groove is a blind end abutting against the guide screw by the pretension force of the return spring; and the guide rod bush is provided with a locking recess for cooperating with the roller to axially lock the button guide rod.

14. The power system for orthopeadic drilling and sawing according to claim 9, wherein the guide rod seats are fixedly arranged in a switch seat, a shifting block spindle is provided along an axis of the shifting block, and the shifting block spindle is arranged in the switch seat and is configured to rotatably cooperate with the switch seat; a shifting block driving handle is provided and is fixedly connected to the shifting block spindle in a circumferential direction, and the shifting block driving handle has two ends being symmetrical with respect to the axis of the shifting block spindle and forming driving ends respectively; and the switch seat is hermetically fixed in the handle housing, the button guide rod extends inwardly to the handle housing and protrudes out of the respective guide rod seat, an end of the button guide rod that protrudes out of the guide rod seat is provided with a sensing head, and the button guide rod sensing member is a sensing circuit board which is located in the handle housing and fixedly connected to the switch seat, and is corresponding to the sensing head.

15. The power system for orthopeadic drilling and sawing according to claim 14, wherein the handle housing is provided with a handheld portion, a cable seat configured for leading in a cable and restraining the same is fixedly connected to a tail end of the handheld portion, a lateral side of an outer surface of a front end of the cable seat is provided with a dovetail sunk platform, and an inner surface of the tail end of the handheld portion is provided with a dovetail sunk groove configured to be interlocked with the dovetail sunk platform; and another lateral side of the outer surface of the front end of the cable seat is fixedly connected to the tail end of the handheld portion via a screw.

16. The power system for orthopeadic drilling and sawing according to claim 11, wherein the power motor is mounted in the handle housing, and a liner tube is coaxially arranged in the hollow shaft of the power motor; and a front end of a claw of the transmission claw has a triangular tooth-shaped structure.

\* \* \* \* \*

UNITED STATES PATENT AND TRADEMARK OFFICE
CERTIFICATE OF CORRECTION

PATENT NO. : 9,924,954 B2
APPLICATION NO. : 14/404598
DATED : March 27, 2018
INVENTOR(S) : Yijun Guo, Xinyun Zhang and Changfeng Liu Page 1 of 1

It is certified that error appears in the above-identified patent and that said Letters Patent is hereby corrected as shown below:

On the Title Page

Item [30]: "2012 1 0494930" to read as — 2012 1 0494930.8 —

In the Claims

Column 10, Line 31, Claim 9: "orthopeadic" to read as — orthopaedic —
Column 10, Line 33, Claim 9: "orthopeadic" to read as — orthopaedic —
Column 10, Line 35, Claim 9: "orthopeadic" to read as — orthopaedic —
Column 10, Line 36, Claim 9: "orthopeadic" to read as — orthopaedic —
Column 10, Line 37, Claim 10: "orthopeadic" to read as — orthopaedic —
Column 10, Line 43, Claim 11: "orthopeadic" to read as — orthopaedic —
Column 10, Line 50, Claim 12: "orthopeadic" to read as — orthopaedic —
Column 10, Line 57, Claim 13: "orthopeadic" to read as — orthopaedic —
Column 11, Line 3, Claim 14: "orthopeadic" to read as — orthopaedic —
Column 12, Line 1, Claim 15: "orthopeadic" to read as — orthopaedic —
Column 12, Line 14, Claim 16: "orthopeadic" to read as — orthopaedic —

Signed and Sealed this
Sixteenth Day of October, 2018

Andrei Iancu
*Director of the United States Patent and Trademark Office*